United States Patent [19]

Fromson et al.

[11] 4,442,494

[45] Apr. 10, 1984

[54] TOOL WEAR AND TOOL FAILURE MONITOR SYSTEM

[75] Inventors: Robert E. Fromson, Wilkins Township, Allegheny County; Lanson Y. Shum, Salem Township, Allegheny County, both of Pa.

[73] Assignee: Westinghouse Electric Corp., Pittsburgh, Pa.

[21] Appl. No.: 322,619

[22] Filed: Nov. 18, 1981

[51] Int. Cl.³ .................... G06F 15/46; G01N 19/02
[52] U.S. Cl. ................................. 364/511; 364/474; 340/680; 73/104
[58] Field of Search ............... 364/184, 185, 474, 475, 364/506, 507, 511, 551; 340/679, 680; 318/563, 565, 572, 650; 73/104, 105; 408/9–13, 16

[56] References Cited

U.S. PATENT DOCUMENTS

| | | | |
|---|---|---|---|
| 3,809,870 | 5/1974 | Auble et al. | 73/104 |
| 4,176,396 | 11/1979 | Howatt | 73/104 |
| 4,207,567 | 6/1980 | Juengel et al. | 73/104 |
| 4,228,514 | 10/1980 | Weiss | 73/104 |
| 4,260,986 | 4/1981 | Kobayashi et al. | 340/680 |
| 4,351,029 | 9/1982 | Maxey et al. | 364/511 |

OTHER PUBLICATIONS

"Investigation of Adaptive Exponential Smoothing Algorithms in Monitoring Tool Wear", by DeVries et al; published in a paper presented at North American Metalworking Research Conf. IX, on pp. 523–527.

"Does Adaptive Control Still Promise Improved Productivity", by Larsen, published in Iron Age, Jul. 27, 1981, pp. 57–68.

Primary Examiner—Gary Chin
Attorney, Agent, or Firm—C. M. Lorin

[57] ABSTRACT

In a computerized numerical control (CNC) or a direct numerical control (DNC) machine tool, the second derivative as a function of time of the net power applied to the cutting tool is used to detect approaching tool failure, and a statistical representation of such occurrences with a series of tools is used to derive instantaneously the percentage of wear experienced by a new tool in terms of the statistically expected critical level of net power.

5 Claims, 10 Drawing Figures

TOOL WEAR AND TOOL FAILURE MONITOR SYSTEM

BACKGROUND OF THE INVENTION

The invention relates to tool wear rate and tool-failure monitoring. The performance of the cutting tool in machine tools and manufacturing processes is most critical to productivity, as stated in Iron Age, July 27, 1981 "Does Adaptive Control Still Promise Improved Productivity" by Raymond J. Larsen, pp. 57-68. In particular, a reliable tool breakage detection system is essential to avoid loss of cutting tolerances, overload and catastrophic failure. Attempts have been made to follow the tool deterioration process, either by direct viewing techniques, by reference to models, or even by material exploration for possible internal flaws.

Another approach to the problem is found in "Investigation of Adaptive Exponential Smoothing Algorithms in Monitoring Tool Wear" by W. R. DeVries, J. F. Raski and J. C. Mazur, a paper presented at North American Metalworking Research Conf. IX, on pp. 523-527.

There, an exponential smoothing algorithm is used to detect any significant deviations from an established trend in the cutting force as it is continuously sensed, e.g. as an indication of changes in the wear pattern as they develop. With such an approach, predictions are in fact made which are based on past measurements.

Another prior art technique disclosed in copending application Ser. No. 100,674, now U.S. Pat. No. 4,351,029 on Dec. 5, 1979, by Maxey et al. relies on net power measurement and derives the integration thereof of a function of time to obtain by reference to experience with a similar tool, the life expectancy of a particular tool, thereby to avoid the critical event once the end of such life expectancy is about to be reached.

In contrast to any of the prior art approaches, the present invention provides (1) for knowing at any given time, for any given tool, under any cutting condition, where the tool is operating, between zero and 100% wear, under its normal life time conditions and (2) for instantaneously detecting, whether such wear rate conditions have been reached which require an immediate shutdown, tool maintenance of changing of tool, thereby to prevent catastrophic tool failure.

The invention also provides for overall monitoring of tool wear and/or tool failure in hydraulically, electromechanically controlled or a computerized installation involving multi-tool and multi-process operation with individual, or centralized control and supervision.

SUMMARY OF THE INVENTION

The invention comprises a method and apparatus for the instantaneous determination of the degree of wear of a particular tool operating with a given workpiece processing cycle, including:

instantaneously deriving the second derivative of net power consumed with each new tool in operation with said processing cycle as a function of time;

simultaneously deriving an indication of the final net power consumed upon the occurrence of a critical gradient in said derived second derivative and an indication of the time interval having lapsed with the operation of the tool until said occurrence;

recurrently establishing from past history with a series of similar tools operating with the same workpiece processing cycle: a statistical final net power and a statistical time interval; and determining instantaneously with the new tool a percentage of said statistical time interval as a representation of the percentage of said statistical final net power, thereby ascertain the degree of wear of said new tool in operation.

The invention also comprises taking protective steps with each new tool operation when a predetermined critical gradient in the second derivative of net power has been reached.

DESCRIPTION OF THE PREFERRED EMBODIMENT

There is a need for tool wear monitoring apparatus that can provide indication of a dull tool generally and independently of prior knowledge of the cutter wear-profile, of the cubic inches of metal removed, and that can display the cutter "condition" as well as trigger the termination of the cutting action before damage is done to the workpiece or under a damaged tool to prevent the workpiece dimensions from going out-of-tolerance.

The present invention is based on the net power vs. time characteristic of a tool in operation, e.g. while the cutting edge is wearing. As explained in the aforementioned Maxey et al. patent application net power is obtained by subtracting the idle power consumed by the spindle rotating the tool without engagement with the workpiece from the total power consumed when the tool is operating.

Figure 1:
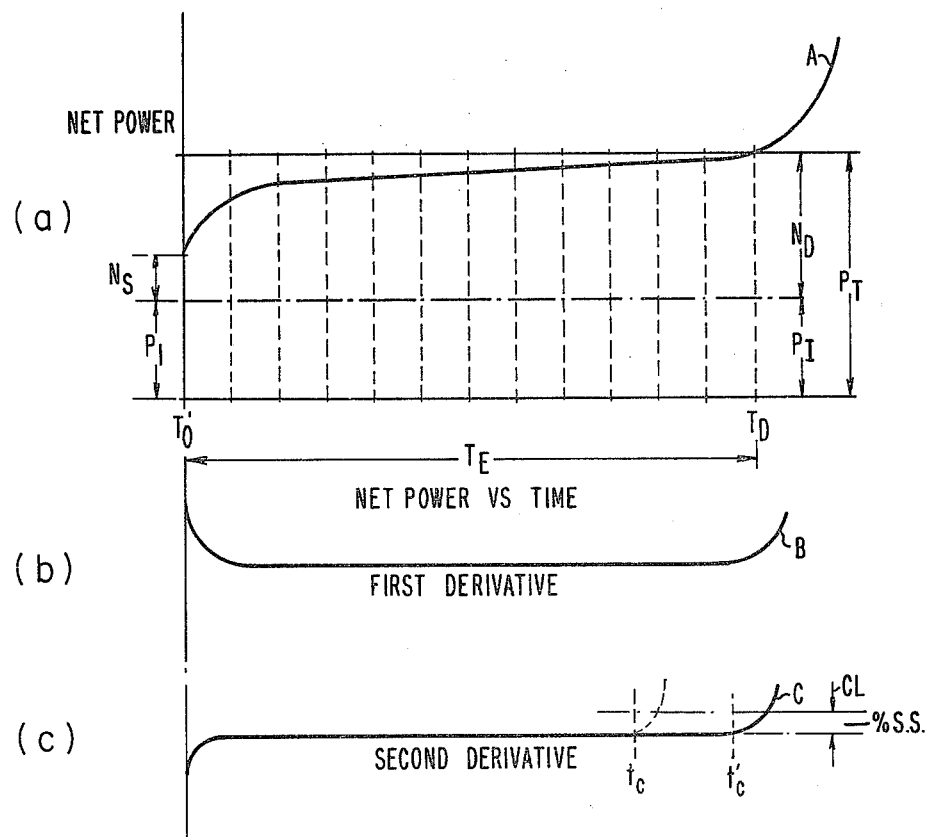
FIG. 1 represents three curves related in time, curve (a) is the net power consumed by a particular tool as a function of time; curve (b) is the first derivative of curve (a); curve (c) is the second derivative of curve (b) used according to the present invention for monitoring tool wear and for anticipating tool failure.

Referring to curve (a) of FIG. 1, net power shown on the ordinate as a function of time indicates how much the cutting edge is losing of its sharpness as long as it is used, continuously or intermittently. This means that the ordinate is increasing with time. Such increase is very much marked at the beginning and at the end of the curve, while there is a linear progression during a major portion of the curve inbetween. As indicated on FIG. 1 the net power characteristic is defined as ($P_T-P_I$) where $P_T$ is the total power consumed when the tool mounted on the rotating spindle is cutting, whereas $P_I$ is the idle power, namely when the tool does not make contact with the workpiece. Initially, at time $T_O$, when the sharpened tool engages the workpiece from the start, net power is $N_S$. At the last stage, when net power has reached the critical stage at instant $T_D$, net power has become $N_D$ which is the power consumed with a dull tool, e.g., a tool which requires maintenance. At the time, the time interval between $T_O$ and $T_D$ is $T_E$. The curve of FIG. 1 is a characteristic curve for the degree of wear of a tool. It reflects the increased cutting force F at radius R from the developing dullness of the cutting tool. Assuming a constant radius R for the workpiece being cut, power (P) can be equated with F by the formula $P=F\times R$, where R is a constant K. Net power, as disclosed in the Maxey et al. application, has been found a more significant parameter than tool power consumed with the spindle and tool of the machine. The initial sharp increase marks the break-in period of the tool when the steady-state shape and geometry of the cutting edge have not been established yet. The linear portion of the curve represents the useful life. Depending upon the workpiece processing cycle, for instance, the nature of the tool and the workpiece, the materials in presence, the cutting depth, the speed, the slope and the useful life may vary from tool to tool. When identical tools are used with identical workpieces in the same workpiece processing cycle, curve (a) will remain of the same order from tool to tool. In such case, since the sharp increase at the end of the curve will occur about at the same time for each tool, it should be possible to warn the operator of the likelihood at such time that the wear rate is so rapidly increasing that a tool failure is imminent and the machine tool should be stopped. To solve this problem as shown in the Maxey et al application, tool failure monitoring has been based on the integral of curve (a), to instantaneously measure the accumulated use and trigger the alarm when it reaches a level corresponding to the life expectancy of the tool.

Figure 2:
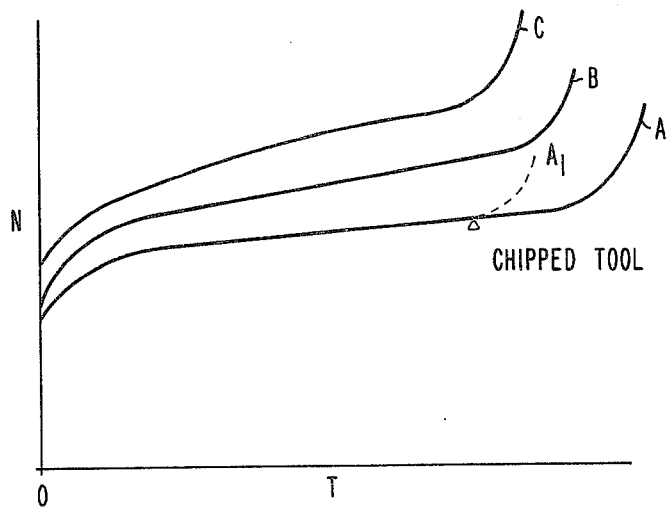
FIG. 2 is a series of curves typically representing net power vs. time which are characteristic of a different machinability, surface speed or tool geometry, metal texture, for instance. An analogous and early departure from the linear progression toward the statistical critical point at the knee of the curve is indicated in dotted line on one of the curves in order to show an anomaly in the operation due for instance to a chipped tool.

The present invention proposes instead not to rely on the life expectancy; but rather to determine instantaneously when the degree of wear has reached a critical level. With this approach, monitorings are based on actuality rather than expectancy. Accordingly, the response of the tool failure monitoring apparatus will be highly reliable as it should at such critical event occurrence. Referring to FIG. 2 which represents a family of curves A,B,C applicable to different tools or workpiece processing cycles, it is of importance also to observe as shown in dotted line for curve A, that tool failure may occur before its normal occurrence based on life expectancy. Such premature catastrophic failure might be caused by material imperfections in the cutting tool, by inclusions of hard spots in the workpiece material. It might also result from anomalous vibrations from the machine and the holding means, or be due to irregular workpiece geometry, or a severe interruption in the cutting process, for instance. These and other anomalies are of major concern to plant operation since they are unpredictable. An early detection of a dull tool condition such as shown at the start of the dotted line of FIG. 2, will either eliminate or reduce such occurrences with minimal consequential cost and less interruptions of shop production. The inventive approach to instant readout of each tool wear condition, needed for efficient machine tool management, will now be explained by reference to curves (b) and (c) of FIG. 1. Curve (b) represents the first derivative and curve (c) is the second derivative function of curve (a).

It appears from curve (b) that the ordinate remains constant during the useful life of the tool, and that the constant ordinate level depends upon the slope of curve (a) in its linear portion. Accordingly, referring to FIG. 2, the first derivative function for curves A, B and C will be at different levels. Referring again to FIG. 1, the initial and final non-linear portions of curve (a) appear in curve (b) to have corresponding non-linear portions one decreasing for the break-in region, the other increasing for the critical wearing condition. In contrast, with the second derivative the curve is most of the time aligned with the abscissa axis, whatever the nature of the original net power curve. Also during the initial as well as the final change of slope, the curve increases from one side to the other of the abscissa axes. This means that signal representative of the curve (c) function will initially be negative, then remain at zero value during most of the tool useful life, and will end to be positive when approaching the knee of curve (a). Moreover, the sharpness of the third curve (c) is in the break-in and in the failure regions substantially increases, thus making detection more quickly responsive. This will be the case in particular upon the encounter of an internal flaw, of a crack developing in the tool or of a chip lost on a hard spot of the workpiece. The accelerated wear caused at such instant will immediately raise the characteristic of curve (c) prematurely as shown in dotted line, thereby causing a detection and the triggering of an alarm. To this effect, the practice will be to select a critical level CL suitable to preclude total failure, as shown in FIG. 1, beyond which all protective measures will be taken such as a shutdown and changing of the tool. Thus, protection is automatically assured at time $t_c$ if there is such a premature failure, or at time $t'_c$ if the tool lasts normally. The critical level CL will be adjustable so that users can design protection for the particular application at hand.

It appears that the second derivative approach overcomes many of the handicaps of the prior art approach to tool monitoring.

Rather than looking for the optimum tool life, the invention aims at anticipating tool failure and at instantaneously knowing the tool condition while it cuts. It is based on the realization that knowing how long a particular tool is expected to have its useful life does not account for every day's experience where a catastrophic failure might occur before the predicted termination of the useful life. Such a failure can result from many circumstances such as a hard inclusion in the metal being cut, an improper heat treatment of the workpiece, an inadequate stiffness of the part or of the fixtures holding the part, a tool anomaly like grinding heat checks, a faulty braze, an inhomogeneity in the tool material like a void or crack, the vibrations of the machine or the spindle. Even in the absence of such adverse factors, it is possible for certain materials to show, when machined by chip-making tools, non-predictable tool wear, e.g. unexpected losses of material removed per tool.

In the machine tool industry tool wear monitoring is most important. The invention, because it provides a constant indication for any tool in any kind of operation of its wear condition and alerts the operator of the unexpected approach into the critical zone, is applicable to any type of machine, electromechanical or not, to numerical control (NC) machines, to computerized numerical control (CNC) machines, or to digital numerical control (DNC) machines, as well as to transfer machines such as mainly used in the automotive and farm equipment manufacturing industry. For multiple tasks, involving such different processes as drilling, milling, turning, grinding, broaching, a random tool failure and un-planned tool changing are not desirable. In this regard, the present invention makes it possible to have remote and local "free-standing" black boxes. This represents a commercial advantage over larger scale computer investment. Such "free-standing" black boxes are applicable to any individual machine. Since a given box need only examine any spindle net power for about 1 second, as many as 60 spindles can be multiplexed to one black box that has read-out, remote the local, as well as spindle/machine remote control. Each such black box will locally respond to the net power consumed and automatically monitor the second derivative thereof. Such "free-standing" monitor will typically be a dedicated micro-computer. Since numerically controlled machines have already the necessary computing power, they will not need the "free-standing" monitor. In such case tool wear monitoring will be provided at minimum cost. Furthermore, these machines are equipped for variable depth-of-cut processes. It becomes possible, then, by proper programming to operate the tool wear monitoring feature on a periodical basis and to detect tool wear at regular intervals for specific depths of cut.

Figure 3:
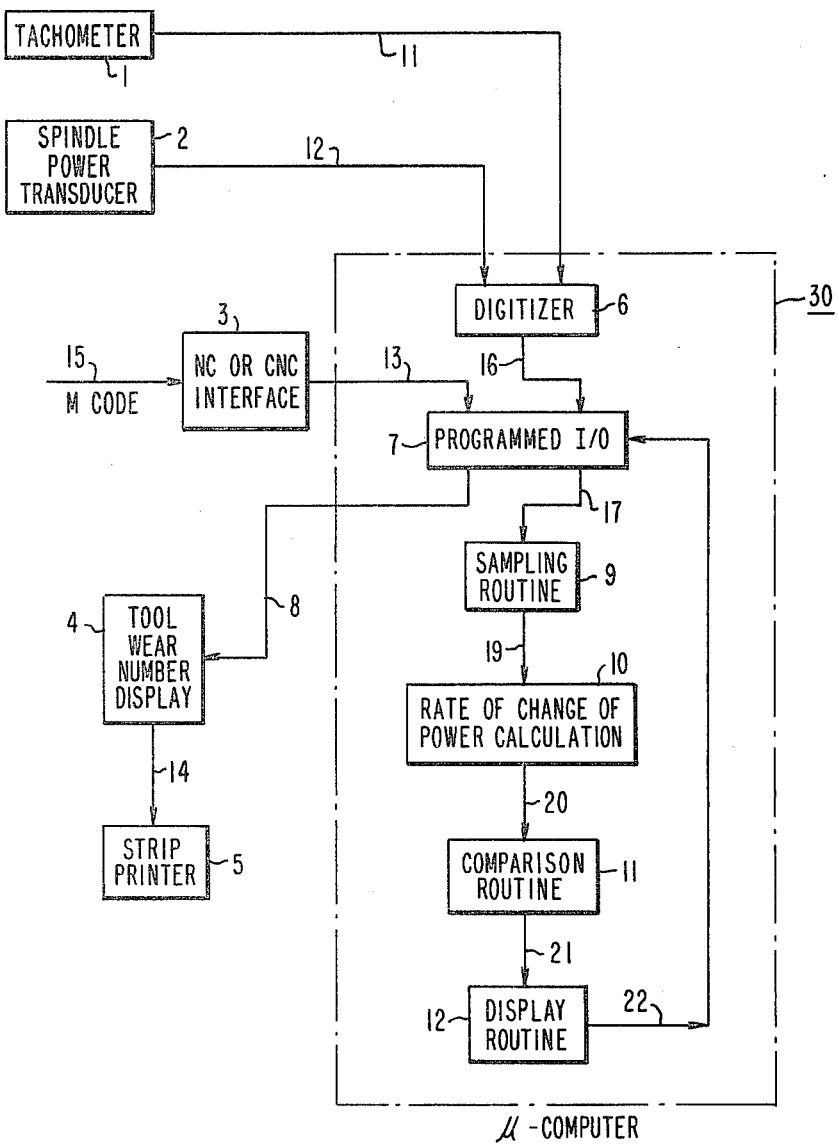
FIG. 3 shows a first embodiment of the tool monitoring system according to the present invention.

Referring to FIG. 3, a microprocessor controlled tool failure monitoring apparatus according to the invention is shown. The apparatus typically operates with net power information instantaneously derived from a combination of actual power consumed and the speed of the spindle carrying the fuel tool if it is a drilling tool, or of the workpiece if the tool is a cutting tool. The analog speed signal is derived on line 11 from a tachometer, while the indication of power on line 12 is derived from a transducer 2. As described in the aforementioned Maxey patent application, idle power is subtracted from the inputted power driving the spindle in order to obtain net power a practical expression of the force exerted by the tool against the workpiece. The speed and power signals are digitized by circuit 6 at the input of a microprocessor 30. The digital signal from circuit 6 are treated when required by the programmed input/output portion 7 of the microprocessor which determines the application of the interval software logic of the microprocessor to the particular tool or tooling under monitoring and provides tool wear status display in circuit 4 which goes by line 14 to the strip printer. The programmed input/output circuit 7 also receives on line 13 a code m characterizing digitally the nature and the number of the tool depending upon whether microprocessor 30 is monitoring the tools under the supervision of a numerical control machine (NC) or of a computerized controlled machine (CNC), the instructions and commands to/and from which are distributed, selected and identified at the interface by circuit 3. A sampling routine 9 is performed iteratively in response to the programmed I/O circuit 7 via by line 17. This routine causes circuit 10 to effect a first and a second derivation based on the net power derived from line 16 for the particular tool monitored as indicated by line 13. Such calculation may be recurrent, or caused to occur at specific sampling instants in accordance with the program of circuit 7. Whenever the second derivative comes to exceed a critical level, this event will be detected by the comparison routine of circuit 11. The display routine 22 will indicate whether the particular tool is operating in the safe zone, e.g. in its useful life, or whether it has entered the critical zone. There will be information fed back by line 22 to the programmed I/O circuit 7 in order to signal completion of the various routine and set routines. By line 8 tool wear status is displayed by circuit 4 and logged in the strip printer 5. The operation of the tool failure monitoring apparatus of FIG. 3 will now be described by reference to FIGS. 4, 5 and 6 which are flow charts of the logic steps controlled by the microcomputer.

Figure 4:
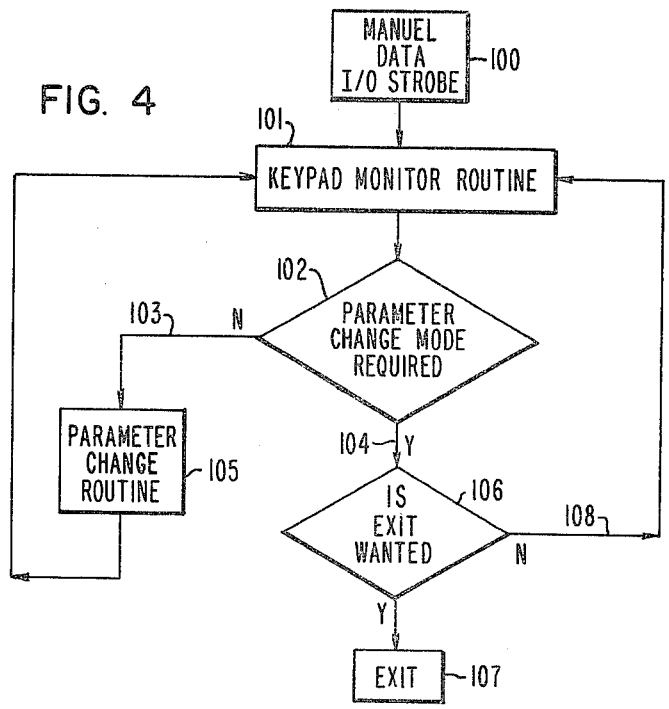
FIGS. 4, 5 and 6 are flow charts illustrating the operation of the tool monitoring system of FIG. 3.

Referring to FIG. 4 a flow chart indicates how a typical multicharacter keypad 100 is able to communicate with the microcomputer and transmit thereto all the parameter settings and satisfy display requirements. This is achieved under a conversational software program, usually supplied by the computer manufacturer. Keypad 100 operates under manual data in the form of the I/O strobe which starts a keypad monitor routine at 101. Thus, upon the occurrence of an interrupt from the keypad, the keypad monitor routine decides at 102 whether the request is for parameter setting along 103 of for output to a display along 104. In the first instance, by 103 the system goes to 105 where the current values are displayed and the parameter setting routine effectuates the change. If there is no parameter setting change required, the system by 104 goes to 106 where the question is whether to start the keypad monitor routine gain namely via 108, or to exit at 107.

Figure 5:
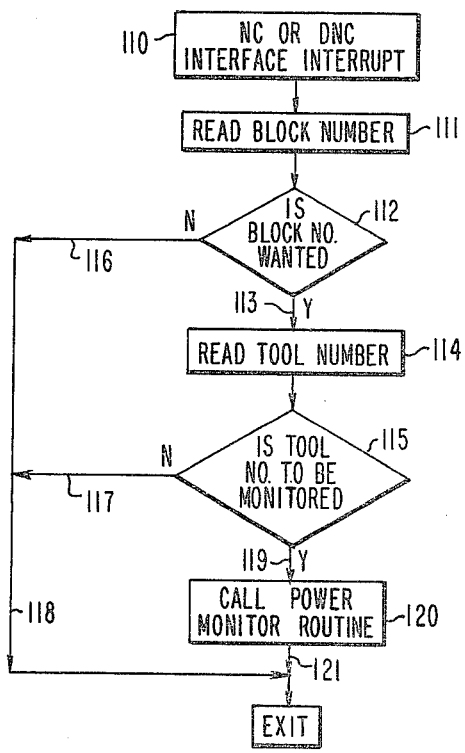
Figure 9:
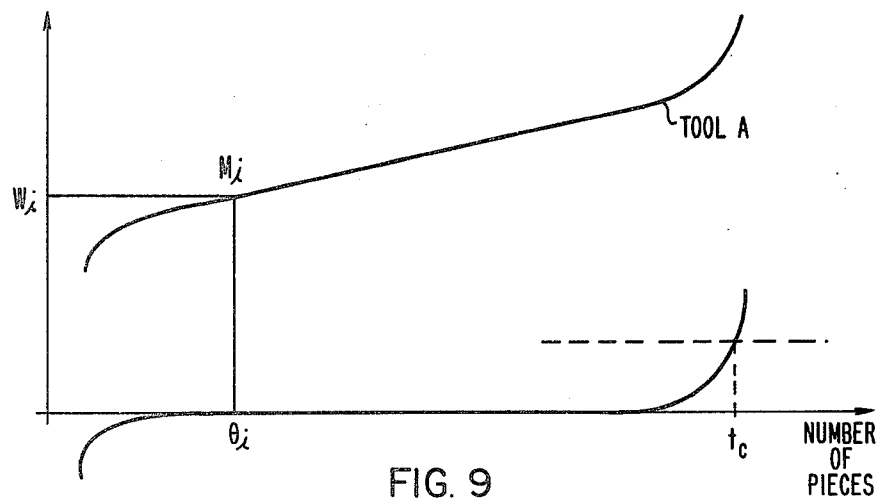
FIG. 9 shows one of a series of identical workpieces typically processed by the same tool during a workpiece processing cycle.

If the system goes to exit, a "Run" mode is performed according to the software chart of FIG. 5. The interface interrupt at 110 is organized so as to respond either within a computerized numerical control (CNC) machine tool system or within a direct numerical control (DNC) machine tool system. The computer of the CNC, or of the DNC, reads the data blocks. Upon reading a data block as interrupt is generated which triggers at 111 the microcomputer to execute the ensuing software. Thus at 111 the microcomputer requests the current block number from the CNC and at 112 compares the block number with those which are under observation to conclude whether such block number is wanted, at 113, or not, at 116. If the block number correctly fits the block number under observation, then, by 113, at 114 the tool number is read from the CNC and is further verified, at 115 where it is asserted whether the tool number relates to the right tool. If it is YES, by 119 the system goes to 120 where the power monitor routine of FIG. 9 is called for. Otherwise, by 117 and 118 the program exits. Also, if at 112 the answer is NO to the question whether it is the right block number, by 116 and 118 the program will exit.

Figure 6:
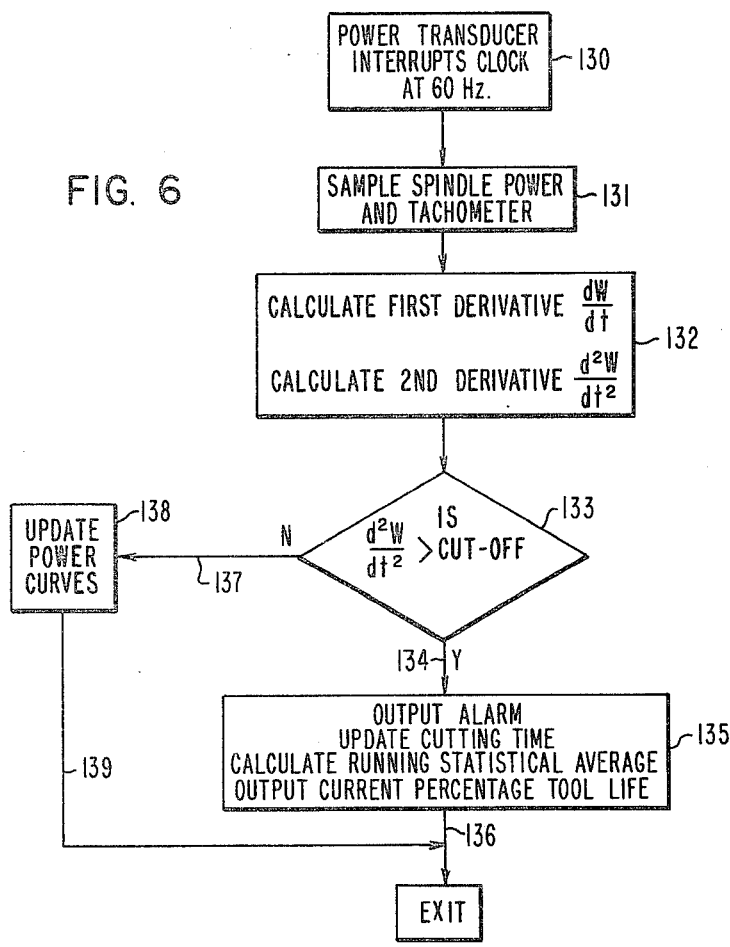

Referring to FIG. 6, the power transducer at 130 interrupts the microcomputer under the 60 Hz clock which is synchronized to the 60 Hz power line supplying the spindle motor drive. Then, at 131 the program obtains a sample of the spindle power and of the spindle speed. Thereafter, the microcomputer effectuates, at 132, the calculation of the net power by subtracting the idle power at the indicated speed from the total power derived from the transducer. Immediately two successive computations are made involving the first and the second derivative of net power.

The next step 133 consists in comparing the second derivative of net power to a preset cut-off level. if the second derivative remains below such preset cut-off level by 137 the power curves of FIG. 1 at 138 are updated. This being done, the system exits by 139. Should, however, at 133 the second derivative exceed the threshold defined by the cut-off level, by 134 the system goes to 135 which provides for outputting an alarm audible or visual. Also, at this moment the cutting time is updated. The curves of FIG. 1 at this stage, and as now recorded, have become history. The system at 135 establishes the tool life, either in terms of lapsed time or in terms of the number of pieces processed by the same tool. This tool life will serve in establishing statistical data for calculating the average tool life. For each tool, when the operator changes it, a new set of curves will be operated.

If the second derivative does not exceed the preset cut-off level at 133, following updating at 138, the microcomputer will accept another interrupt 1/60 second later. The loop will be run continuously until the CNC reads another block number at 111 according to the flow chart of FIG. 8. All the power curves shown in FIG. 1 will have a running average for the complete block of NC move.

Figure 7:
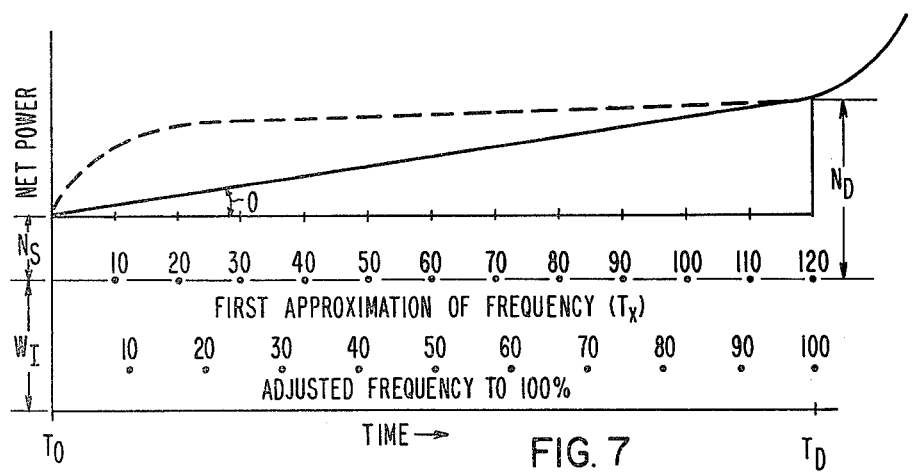
FIG. 7 is the net power vs. time curve of FIG. 1 established by a statistical determination of the critical ordinate and abscissa of the knee on the curve for a series of identical tools operating with the curve workpiece processing cycle. As explained hereinafter, the percentage of wear at any instant with a new tool is read directly from a linear progression up to the critical point at the knee of the curve.

Referring to FIG. 7, a net power tool characteristic is shown in dotted line extending over the useful life known from past experience with similar tools and under the same workpiece processing cycle. As earlier explained it is possible that one particular tool reaches the critical zone prematurely. It is also possible that tool failure occurs after a useful life longer than expected. The net power tool characteristic of FIG. 7 is a statistical representation of all the occurrences with many tools. The curve represents an accumulation of data following detection with the tool failure monitoring system of FIG. 3. Therefore, the critical level CT has been readied so many times at an instant such as $t_c$, or $t'_c$ of FIG. 1.

Except for such accumulation of statistical data, the curve of FIG. 7 is the same as the curve of FIG. 1. The amount of net power initially is $N_S$ as statistically determined. So is the amount of net power $N_D$, reached when the level CT has been needed, also a statistical value. Also, $T_D-T_O$ is the useful life of the tool determined by repeated cycles with different tools. Thus, each time the tool failure monitoring apparatus of FIG. 3 has been used to detect when the tool has become dull and there is a serious risk of failure. The statistical data are established, preferably, with the three sigma (3$\sigma$) method. According to the classical gaussian profile, most of the values of $N_D$ and $T_D$ will be centered in the middle of all of the other values. Reference values will be discarded. Thus, anomalous failures due to hard spots and broken chips will not be recorded for the purpose of updating the curve of FIG. 7. It is also chosen to count the updated time interval as hundred units of time, as shown on the lower abscissa axis of FIG. 7. Thus, if updating of previous data leads to a longer time interval, say of 120 units of time as shown on the upper abscissa axis, the net statistical value will be considered as 100 unit again.

FIG. 7 shows also a straight line joining the initial point at time $T_O$ on the curve to the final point at time $T_D$ on the curve. It appears that with a new tool, based on the statistical lines, at any instant, the units of time which have lapsed indicate a percentage of $(N_D-N_S)$, e.g. a percentage of wear.

Figure 8:
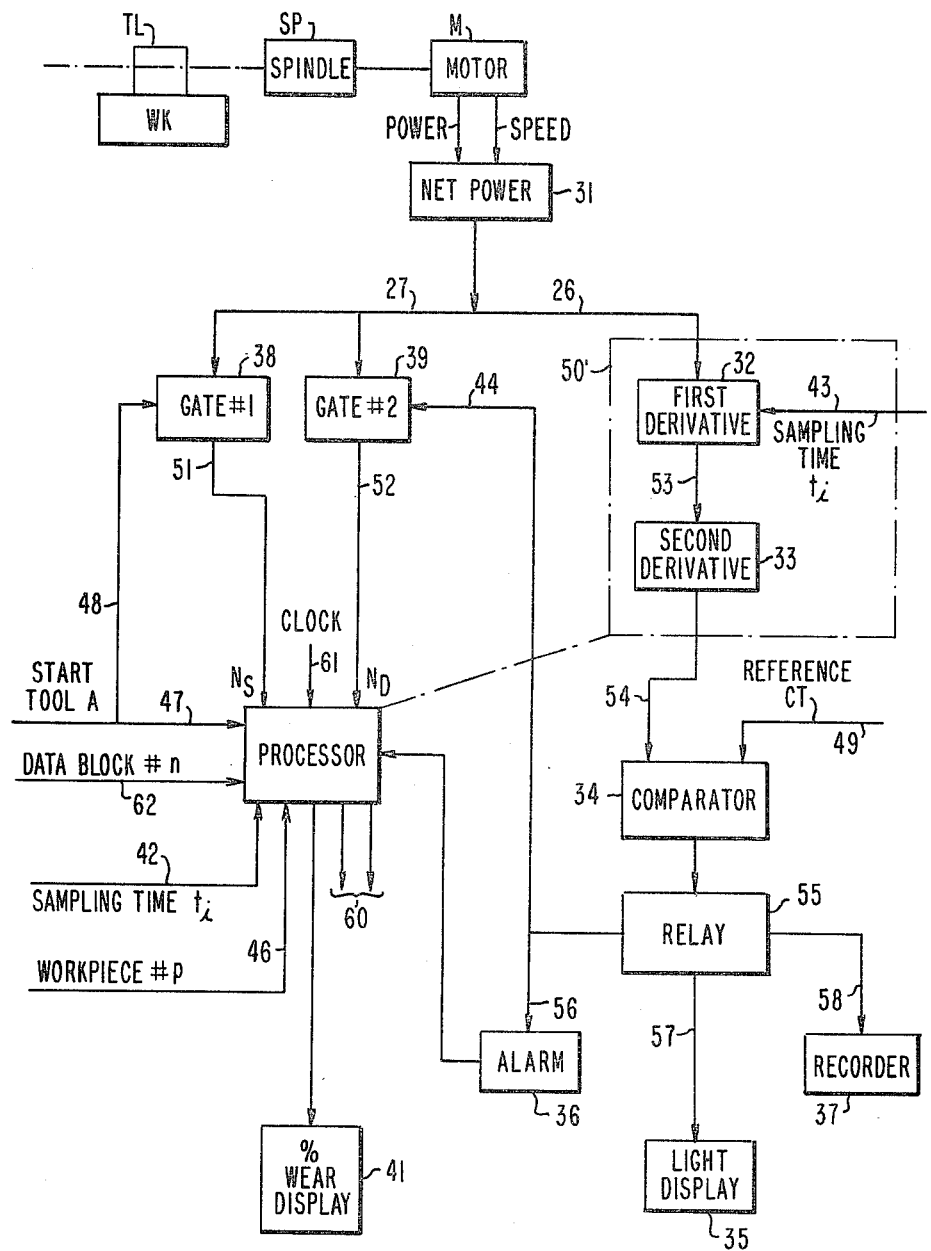
FIG. 8 shows another embodiment of the tool monitoring system according to the present invention.

FIG. 8 shows the tool wear rate monitoring feature incorporated in a tool failure monitoring apparatus like the one of FIG. 3.

Like in FIG. 3, net power as a function of power and speed is derived (at 31) and the first and second derivative are provided (at 32 and 33, respectively) by a microprocessor (50'). A comparator 34 responds to the second derivative on line 54 from 33 and to the reference level CT on line 49. When the threshold level CT is reached a relay 55 actuates by line 56 an alarm 36, by line 57 a light display unit 35 and by 58 a recorder 37. The first derivative is obtained during a sampling time $T_i$ obtained from line 43. FIG. 8 also shows the hardware and processing unit for the pecentage wear tool monitoring feature of FIG. 7. In this regard, net power from 31 on line 27 is applied to a first gate 38 and a second gate 39. The first gate is triggered, when tool A is started, by line 48. At the same time the processor 50 is conditioned by lines 47 and 51 for the initial operative step. Gate #1 at this time passes the value $N_S$ derived from block 31. When relay 55 is actuated at time $T_D$, by line 44, the second gate 39 is triggered to supply the value $N_D$ of net power to the processor. Accordingly, processor 50 will establish the statistical update of $(T_D-T_O)$ and of $(N_D-N_S)$, and the units of time, related to the clock signal of line 61, are adjusted to 100 for such updated time interval $(T_D-T_O)$. Accordingly, when a new tool is being set into operation, the % of wear is automatically displayed by block 41 as explained in relation to FIG. 7. More generally, in a computerized numerical control machine, the computer will follow the processing cycle by digital treatment of incoming data blocks such as at 62 on FIG. 8, for the particular workpiece number, such as at 46, for the particular tool such as at 47, during sampling times $t_i$ such as at 42. Commands and status signals will be sent to the system by lines such as 60.

To summarize: The following procedure is applicable to constant depth-of-cut, constant feed rate situations, such as found in many metal removal processes. Furthermore, this procedure will be a periodic monitoring function, i.e., it is not necessary to provide full time monitoring. Typically, a one second data monitoring window will be sufficient to acquire meaningful data, so multiplexing a single monitor can handle some fifty spindles. In the case of variable stock conditions typically found with N/C contour machining, it will be necessary for the N/C program to specify a constant depth-of-cut, constant feed rate cut at the monitoring intervals.

At the start of the cut, $(T_O)$, extract $N_S$ from $P_T$, and start a variable frequency clock running at an assumed frequency, $(T_X)$. Retain $N_S$ in memory.

As the cut proceeds, at each monitoring interval, I, $N_I$ is extracted and the first derivative and then the second derivative are processed, and the second derivative is compared with prior data points. The second derivative will be "flat" during the gradual wear period and evidence a sharp rise at the knee in the net power vs. time curve. This rise can be detected at selected "risk" levels as a percentage of the steady-state level of the second derivative value.

When the dull tool detector "alarms," it can be used to turn off the machine, thus preventing catastrophic failure. It also has a part to play in the tool wear monitor part of the system.

At the point of dull tool detection, two activities take place, manually or automatically. The value of $N_D$ is displayed and recorded either by dial manipulation or by data processing techniques. The variable frequency time axis is adjusted to readout 100% for the dull tool occurrence point. This can be accomplished manually or by data processing techniques. When manual techniques are employed, the operator can arrive at mental running averages. When data processing techniques, are employed, $3\Sigma$ limits can be derived and used.

Referring to FIG. 7, one can see by example that the first approximation ($T_K$) used by the operator resulted in 120% of dull tool time. When the variable frequency clock is adjusted to 100% at $N_D$, and when the value of $N_S$ is subtracted from $N_D$, a right triangle with an angle $\theta$ is established. Given this proportional relationship, tool wear monitoring can be displayed by a readout of the frequency between 0 and 100 units.

Figure 10:
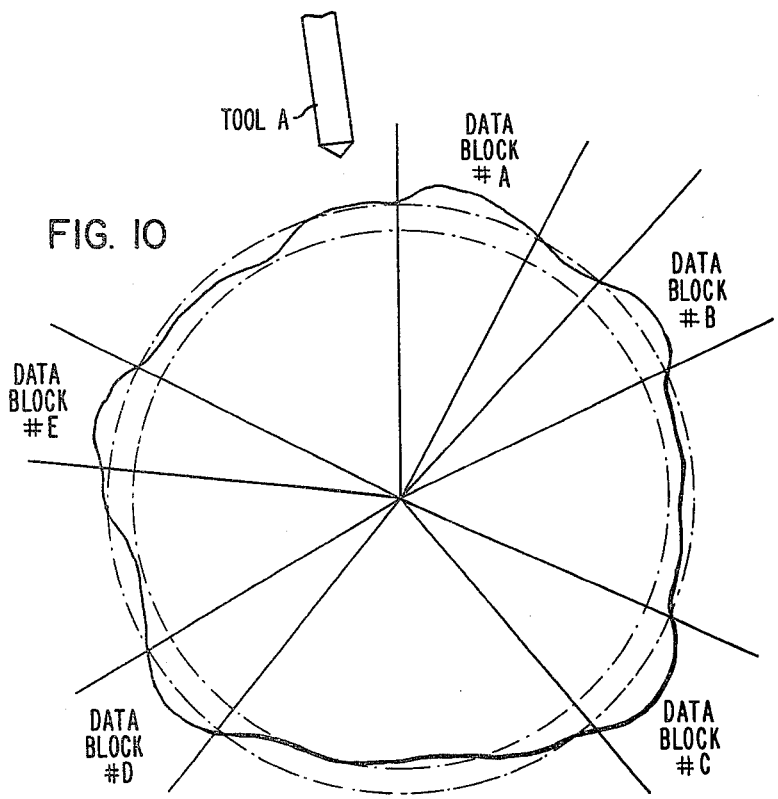
FIG. 10 is the net power curve of FIG. 1 as derived with one tool for a series of processed workpieces.

Referring to FIG. 9 the net power characteristic of FIG. 1 or 7 is shown to illustrate the operation of the apparatus of FIG. 3 or 8, where the same tool is utilized for repeated identical and completed working operations over a large number of identical workpieces. FIG. 10, typically shows one of such workpieces WK as the tool is being rotated in front of the workpiece. For each pass of the tool, due to the different radial dimensions of the workpiece, the tool is encountering a different working zone at the surface of the workpiece, and the zones are separated by voids. In accordance with the present invention, net power is derived by the monitoring system while the tool is cutting material, while a centralized computer determines for each successive cutting depth the metal cutting process profile as a function of time.

In order to carry out the monitoring method based on the net power vs. time characteristic of the tool of FIG. 1 a measurement is made at chosen sampling times $t_i$ which correspond to the same stage of the processing cycle and the value of ($P_T - P_j$) is recorded as a point on the characteristic curve of FIG. 9. Thus, with each additional piece net power is increasing according to the wear rate indicated by the slope of the curve. For each sampling time $t_i$ net powered is derived within the same data block read by the computer. FIG. 10 shows data blocks A through E related to selected zones encountered by the tool on the workpiece successively on each pass. The computer identifies these data blocks and records the net power consumed at the sampling instant in each block. FIG. 9 typically shows the increase of the net power along the working process from one data block to the next. The value $W_i$ at instant $t_i$ determines the point $M_i$ on the characteristic.

It is understood that, while the invention has been described in the context of a cutting tool, the term cutting should be interpreted more generally as the operation of a machine tool including: grinding, extruding, drawing, broaching, turning, as well as milling or boring.

We claim:

1. A method of monitoring tool failure with a machine tool operating with a workpiece comprising the steps of:
    deriving a time related indication of the force exerted by said tool on said workpiece in operation;
    deriving the rate of change of said force as a function of time;
    deriving the second derivative as a function of time of said forces;
    detecting a zero value in said second derivative as an indication of normal tool use; and
    detecting a deviation from said zero value by a predetermined amount as an indication of possible tool failure.

2. A tool failure monitoring apparatus for a machine tool operating with a workpiece comprising:
    means for deriving an indication of the force exerted by said tool on said workpiece in operation;
    a microprocessor for computing the first and second derivative of said indication of force as a function of time; and
    comparator means actuated by said microprocessor for indicating a critical event when said second derivative exceeds a predetermined reference level.

3. A numerical controlled machine tool for operating a plurality of tools with a plurality of workpieces comprising:
    means associated with each of said tools in operation with a corresponding workpiece for deriving respective instantaneous values of net power applied to operate a given tool with a given workpiece;
    central processor means for deriving the second derivative of net power for each of said instantaneous values;
    comparator means responsive to each of said instantaneous values and for each of said tools for deriving a critical signal when the second derivative exceeds a reference level;
    diagnostic means for determining with said comparator means and in response to a critical signal therefrom, any of said tools should be maintained.

4. A computerized numerically controlled machine tool system controlling a plurality of machine tools operating each with at least one tool and an associated workpiece comprising:
    central processor means for controlling the individual operation of said machine tools;
    individual means associated with each tool for deriving an indication of net power applied between such tool and the associated workpiece;
    individual microprocessor means responsive to said indication of net power and associated with a corresponding machine tool for calculating the second derivative of net power and for detecting an increase of the net power second derivative beyond a critical level for generating an alarm signal regarding an operative tool; and
    means responsive to said alarm signal for stopping the operation of the machine tool with respect to said operative tool.

5. Wear rate tool monitoring method for the instantaneous determination of the degree of wear of a particular tool operating with a given workpiece processing cycle, including the steps of:
    instantaneously deriving the second derivative of net power consumed with each new tool in operation with said processing cycle as a function of time;
    simultaneously deriving an indication of the final net power consumed upon the occurrence of a critical gradient in said derived second derivative and an indication of the time interval having lapsed with the operation of the tool until said occurrence;
    recurrently establishing from past history with a series of similar tools operating with the same workpiece processing cycle; a statistical final net power and a statistical time interval; and determining instantaneously with the new tool a percentage of said statistical time interval as a representation of the percentage of said statistical final net power, thereby ascertain the degree of wear of said new tool in operation.

* * * * *